United States Patent [19]
Jamieson et al.

[11] Patent Number: 5,585,475
[45] Date of Patent: Dec. 17, 1996

[54] CALMODULIN-BINDING PEPTIDES AND NUCLEIC ACIDS ENCODING THEM

[75] Inventors: Gordon A. Jamieson; John R. Dedman; Marcia A. Kaetzel, all of Cincinnati, Ohio

[73] Assignee: Chiron Corporation, Emeryville, Calif.

[21] Appl. No.: 268,251

[22] Filed: Jun. 28, 1994

Related U.S. Application Data

[63] Continuation of Ser. No. 831,219, Feb. 6, 1992, abandoned.

[51] Int. Cl.⁶ .............. C07K 7/08; C07K 7/06; C07K 14/00
[52] U.S. Cl. .......... 536/23.1; 536/23.4; 530/324; 530/325; 530/326; 530/327; 530/328; 530/350; 930/250
[58] Field of Search ................. 530/324–328, 530/350; 514/2, 12–16; 536/23.1, 23.4

[56] References Cited

U.S. PATENT DOCUMENTS 5,182,262  1/1993  Leto .................................. 514/13

OTHER PUBLICATIONS

Simon, R. J., et al. (1992) Proc. Natl. Acad. Sci. USA 89: 9367–71.
Devlin, J. J., et al. (1990) Science 249:404–06.
Kaetzel, M. A., et al. (1987) J. Biol. Chem. 262: 3726–9.

*Primary Examiner*—David L. Fitzgerald
*Attorney, Agent, or Firm*—Grant D. Green; Robert P. Blackburn

[57] ABSTRACT

Peptides capable of binding calmodulin are disclosed. The peptides surprisingly do not exhibit strict α-helical conformations.

6 Claims, No Drawings

CALMODULIN-BINDING PEPTIDES AND NUCLEIC ACIDS ENCODING THEM

This application is a continuation of application Ser. No. 07/831,219, filed 6 Feb. 1992, now abandoned.

DESCRIPTION

1. Technical Field

This invention relates to the fields of peptide chemistry and cellular biology. More specifically, the invention relates to peptides which bind to calmodulin and methods for using such peptides.

2. Background of the Invention

Calmodulin is a calcium-binding regulatory protein found in all eukaryotic cells, and is highly conserved across species. The protein has four $Ca^{++}$ binding sites, and contains about 150 amino acids. Calmodulin is responsible for most known calcium-regulated intracellular signals, and regulates a variety of protein kinases, phosphodiesterases, nicotine amide adenine dinucleotide kinase, adenylate cyclase, and others.

The involvement of calmodulin in cell division, proliferation, and metabolism makes it an attractive target for researchers investigating treatment of proliferative disorders such as cancer. Pero, EP 305,008 described the use of calmodulin antagonists to increase the effectiveness of chemotherapeutic agents. Materazzi et al, DE 3,410,848 disclosed the use of calmodulin inhibitors to inhibit metastasis. Cormier, U.S. Pat. No. 4,578,379 disclosed the use of calmodulin-binding compounds to prevent pregnancy. Japanese application JP 1006294 disclosed a number of peptides which specifically inhibit calmodulin, for use in treating heart disease, hypertension, thrombosis, and tumor growth.

Calmodulin binds to a wide variety of proteins. It is currently thought to bind to an amphipathic/amphiphilic α-helical structure. For example, S.M. Roth et al., *Biochem* (1991) 30:10078–84, used NMR to determine helical structure in a complex formed from calmodulin and smooth muscle myosin light-chain kinase. B. Precheur et al., *Eur J Biochem* (1991) 196:67–72 reported that the calmodulin-binding domain of *Bordetella pertussis* adenylate cyclase tends to form an amphipathic helix. J.A. Cox et al., *J Biol Chem* (1985) 260:2527–34 reported the preparation of basic, amphiphilic α-helices which bind calmodulin. M.A. Stevenson et al., *Mol Cell Biol* (1990) 10:1234–38 reported that the 70 kDa heat shock proteins contains a calmodulin-binding domain with α-helical character. K.T. O'Neil et al., *Science* (1987) 236:1454–56 reported the determination of helicity in a calmodulin-binding peptide by sequentially replacing each amino acid with tryptophan, and studying the resulting change in fluorescence.

A number of synthetic calmodulin-binding peptides have been designed: W.F. DeGrado et al., *J Cell Biochem* (1985) 29:83–94; T. Lorca et al., *EMBO J* (1991) 10:2087–94; R.B. Pearson et al., *Peptide Res* (1991) 4:147–57; A. Enyedi et al., *J Biol Chem* (1991) 266:8952–56; K.K.W. Wang et at., *J Biol Chem* (1991) 266:9078–85.

DISCLOSURE OF THE INVENTION

One aspect of the invention is a family of calmodulin-binding peptides which are unusual because they do not follow current predictions that calmodulin-binding peptides should adopt a strict α-helical conformation. Furthermore, many of the calmodulin-binding peptides contain a Trp residue to which is juxtaposed a Pro residue.

Another aspect of the invention is the use of a peptide of the invention to inhibit the activity of calmodulin in a eukaryote.

Another aspect of the invention is an antibody modified to contain a calmodulin-binding sequence of the invention. Another aspect of the invention is the use of calmodulin-binding peptides, modified antibodies, peptide fragments, or analogs to treat tumors or infection; control cell growth, division, and meiosis; regulation of cell motility, sperm motility, and smooth muscle motility; regulation of carbohydrate metabolism; regulation of neurotransmission; antipsychotic activity; anti-inflammatory activity; regulation of secretory processes; and regulation of fluid secretion.

Another aspect of the invention is a biologically-active protein modified to contain a calmodulin-binding peptide sequence, particularly a protein modified to contain a calmodulin-binding peptide sequence such that calmodulin obscures the active site of said protein when bound to said calmodulin-binding peptide sequence.

MODES OF CARRYING OUT THE INVENTION

A. Definitions

The term "calmodulin-binding peptide" refers to peptides or proteins having one or more of the sequences selected from the group consisting of:

SFKQLVTEVFLQSRH (SEQ ID NO. 1); PWLKIRDSLQLNYLP (SEQ ID NO. 2); GSWLQLLNLMKQMNN (SEQ ID NO. 3); ASWTTVRSHFGSTMQ (SEQ ID NO. 4); QLSWKALVTSVLSPT (SEQ ID NO. 5); LSELWRNYSVRLMSS (SEQ ID NO. 6); AQLNRWKSLSKTMMS (SEQ ID NO. 7); TPSTSKWHQLIKSHR (SEQ ID NO. 8); ISLPQLKWLTHRLKQ (SEQ ID NO. 9); FPLLPYTWMARHHGS (SEQ ID NO. 10); NLTPQYFKKWQDLTK (SEQ ID NO. 11); TSSLRNTLQYWRSLI (SEQ ID NO. 12); WPSLTEIKTLSHFSV (SEQ ID NO. 13); WPSISTLSTYTHSLH (SEQ ID NO. 14); WPSIHHMSHLLYSTY (SEQ ID NO. 15); WPSVRTILNTDLLHP (SEQ ID NO. 16); WPSPTRVISTTYFGS (SEQ ID NO. 17); WPSPHKIMSTLQYLR (SEQ ID NO. 18); WPTTRELRSLKSFLT (SEQ ID NO. 19); WPKMTALQSTMKYVT (SEQ ID NO. 20); WPKSFLMWMPKATQL (SEQ ID NO. 21); WPRLSTLASMTNKAI (SEQ ID NO. 22); WPRVKDLSTYLEGHV (SEQ ID NO. 23); PWPMLKQLRLLKSSL (SEQ ID NO. 24); PMNWPTVHAIRSLRK (SEQ ID NO. 25); HISWPTLAQMSLMNF (SEQ ID NO. 26); LAHWPPVKTVLRSFT (SEQ ID NO. 27); VTKWPNLTQLRMLAT (SEQ ID NO. 28); and GSTNRWPTVAKLMST (SEQ ID NO. 29) (in single letter amino acid code).

The term "modified" as used herein in conjunction with an antibody or other protein refers to the insertion or attachment of a calmodulin-binding peptide sequence by chemical or recombinant means. "Chemical means" includes any covalent attachment of the calmodulin-binding peptide to the protein of interest, e.g., using glutaraldehyde or other cross-linking reagents known in the art. "Recombinant means" entails modification of DNA (or other oligonucleotide) encoding the protein of interest to include an oligonucleotide encoding the calmodulin-binding peptide sequence, e.g., by site-specific mutation or other methods known in the art.

The term "inhibit" as used herein refers to the detectable reduction and/or elimination of a biological activity exhibited by calmodulin in the absence of a calmodulin-binding peptide of the invention.

The term "effective amount" refers to that amount of composition necessary to achieve the indicated effect. The term "treatment" as used herein refers to reducing or alleviating symptoms in a subject, preventing symptoms from worsening or progressing, inhibition or elimination of the causative agent, or prevention of the infection or disorder in a subject who is free therefrom. Thus, for example, treatment of a cancer patient may be reduction of tumor size, elimination of malignant cells, prevention of metastasis, or the prevention of relapse in a patient who has been cured. Treatment of infection includes destruction of the infecting agent, inhibition of or interference with its growth or maturation, neutralization of its pathological effects, and the like.

The term "infection" as used herein includes infection by bacteria, fungi, and other parasites, such as leishmania and malarial parasites. "Infectious agents" within the scope of this invention include yeasts and fungi such as *C. albicans* and *P. carinii*; parasites such as malarial *Plasmodia*, giardia, nematodes, roundworms and the like.

The term "hyperproliferative disorder" refers to disorders characterized by an abnormal or pathological proliferation of cells, for example, cancer, psoriasis, hyperplasia and the like.

The terms "amphiphilic" and "amphipathic" denote an α-helical peptide structure having charged (hydrophilic) residues along one surface, and uncharged/hydrophobic residues along the opposite surface.

The term "active fragment" refers to a peptide having only a portion of the one of the sequences identified herein, wherein said portion is sufficient to effect binding to calmodulin at a $K_d$ of $\leq 50$ nm under physiological conditions. Active fragments of the peptides of the invention are expected to have at least four consecutive amino acids from any single peptide, preferably from four to eight residues, more preferably up to ten residues. It is currently expected that the minimal active fragment, for most of the peptides disclosed herein, will include the "WP" dipeptide.

The term "analog" as used herein refers to peptides which exhibit calmodulin-binding activity ($K_d$ of <50 nm under physiological conditions), but differ from the sequences reported herein by conservative substitution of one or two amino acids with other amino acids or amino acid substitutes. Conservative amino acid substitutions are those that preserve the general charge, hydrophobicity/hydrophilicity, and/or steric bulk of the amino acid substituted, for example Gly⇌Ala; Val⇌Ile⇌Leu; Asp⇌Glu; Lys⇌Arg; Asn⇌Gln; and Phe⇌Trp⇌Tyr. Analogs should exhibit the same general structure as the native calmodulin-binding peptide, e.g., as predicted by Chou-Fasman rules (P.Y. Chou & G.D. Fasman, *Biochem* (1974) 13:222–45). "Analog" also includes peptides having one or more peptide mimics ("peptoids"), such as those described in PCT application US91/04282. The presently preferred analog has the sequence WPSLKQLRSLK (SEQ ID NO. 30).

The term "pharmaceutically acceptable" refers to compounds and compositions which may be administered to mammals without undue toxicity. Exemplary pharmaceutically acceptable salts include mineral acid salts such as hydrochlorides, hydrobromides, phosphates, suffates, and the like; and the salts of organic acids such as acetates, propionates, malonates, benzoates, and the like.

The term "ester" refers to moieties of the form $R_1$—C(=O)—$OR_2$, where either $R_1$—C(=O)—O— or $OR_2$ represents a free carboxylic acid group present in the calmodulin-binding peptide, and the other portion represent an esterifying group. Exemplary esterifying groups useful with carboxylic acid groups present in the calmodulin-binding peptide include, without limitation, lower alkyl such as methyl, ethyl, propyl, butyl, hexyl, and the like; lower alkenyl such as propenyl, butenyl, and the like; aryl and arylalkyl such as phenyl, benzyl, naphthyl, and the like; and other groups, such as acetoxymethyl ($CH_3C(=O))CH_2$—); and the like. Exemplary esterifying groups useful with hydroxy groups appearing the in the calmodulin-binding peptide include, without limitation, lower acyl such as acetyl, propionyl, butyryl, benzoyl, and the like.

The term "anhydride" refers to a compound which results from the condensation of two carboxylic acids: $R_1$—C(=O)—O—C(=O)—$R_2$. Anhydrides are formed by condensing carboxylic acids such as acetic acid, propionic acid, benzoic acid, and the like, with a free carboxylic acid group present in the calmodulin-binding peptide. In general, one of the carboxylic acids is "activated", typically by conversion to an acyl halide. For example, acetic anhydrides may be prepared by reaction acetyl chloride with the calmodu- lin-binding peptide of the invention. Formation of anhydrides may require protection of labile groups present in the peptide using standard protecting groups.

The term "amide" as used herein refers to moieties of the form $R_1$—C(=O)—$NR_3$, where either $R_1$—C(=O)— represents a free carboxylic acid group present in either the calmodulin-binding peptide or the amidating group, and $NR_2R_3$ represent an amine present in the amidating group or calmodulin-binding peptide. Exemplary amidating groups useful with carboxylic acid groups present in the calmodulin-binding peptide include, without limitation, lower alkylamine such as methylamine, ethylamine, dimethylamine, butylamine, N-methyl-N-ethylamine, and the like. Exemplary amidating groups useful with amine groups appearing the in the calmodulin-binding peptide include, without limitation, lower acyl such as acetyl, propionyl, butyryl, benzoyl, and the like.

The term "oligonucleotide" as used herein refers to DNA, RNA, and the like, which is capable of encoding a calmodulin-binding peptide of the invention. Oligonucleotides may be either single- or double-stranded.

B. General Method

The peptides of the invention were identified by screening a coliphage M13 library (J.J. Devlin et al., *Science* (1990) 249:404–06) for pIII phage proteins containing an epitope binding to calmodulin immobilized on a solid support. The phages were applied to a calmodulin-Sepharose® column, and eluted with EGTA. The phages isolated by this procedure were then subcloned and sequenced to determine the amino acid sequence of the binding peptide. All but one of the peptides so identified contain tryptophan (W). In 26 of 30 cases, the peptides also contain proline (P) and/or glycine (G), which are known to inhibit helicity of peptides. In 17 of 30 peptides, the sequence WP occurs at or near the N-terminus.

The peptides of the invention comprise the following sequences:

SFKQLVTEVFLQSRH (SEQ ID NO. 1); PWLKIRDSLQLNYLP (SEQ ID NO. 2); GSWLQLLNLMKQMNN (SEQ ID NO. 3); ASWTTVRSHFGSTMQ (SEQ ID NO. 4); QLSWKALVTSVLSPT (SEQ ID NO. 5); LSELWRNYSVRLMSS (SEQ ID NO. 6); AQLNRWKSLSKTMMS (SEQ

ID NO. 7); TPSTSKWHQLIKSHR (SEQ ID NO. 8); ISLPQLKWLTHRLKQ (SEQ ID NO. 9); FPLLPYTWMARHHGS (SEQ ID NO. 10); NLTPQYFKKWQDLTK (SEQ ID NO. 11); TSSLRNTLQYWRSLI (SEQ ID NO. 12); WPSLTEIKTLSHFSV (SEQ ID NO. 13); WPSISTLSTYTHSLH (SEQ ID NO. 14); WPSIHHMSHLLYSTY (SEQ ID NO. 15); WPSVRTILNTDLLHP (SEQ ID NO. 16); WPSPTRVISTTYFGS (SEQ ID NO. 17); WPSPHKIMSTLQYLR (SEQ ID NO. 18); WPTTRELRSLKSFLT (SEQ ID NO. 19); WPKMTALQSTMKYVT (SEQ ID NO. 20); WPKSFLMWMPKATQL (SEQ ID NO. 21); WPRLSTLASMTNKAI (SEQ ID NO. 22); WPRVKDLSTYLEGHV (SEQ ID NO. 23); PWPMLKQLRLLKSSL (SEQ ID NO. 24); PMNWPTVHAIRSLRK (SEQ ID NO. 25); HISWPTLAQMSLMNF (SEQ ID NO. 26); LAHWPPVKTVLRSFT (SEQ ID NO. 27); VTKWPNLTQLRMLAT (SEQ ID NO. 28); and GSTNRWPTVAKLMST (SEQ ID NO. 29)

Preferred calmodulin-binding peptides of the invention contain the WP dipeptide.

The sequences may be embedded in the sequence of longer peptides or proteins, as long as they are accessible to calmodulin. Proteins or peptides containing the calmodulin-binding sequences may be selected for specificity to particular tissues and/or organisms, e.g., by following the procedure described in the Example below.

The peptides of the invention may be prepared by standard peptide synthesis techniques, such as solid-phase synthesis. Alternatively, the sequences of the invention may be incorporated into larger peptides or proteins by recombinant methods. This is most easily accomplished by preparing a DNA cassette which encodes the sequence of interest, and ligating the cassette into DNA encoding the protein to be modified at the appropriate site. The sequence DNA may be synthesized by standard synthetic techniques, or may be excised from the phage pIII gene using the appropriate restriction enzymes.

Fragments of the calmodulin-binding peptides identified herein may be prepared by simple solid-phase techniques. The minimum binding sequence may be determined systematically for each calmodulin-binding peptide by standard methods, for example, employing the method described by H.M. Geysen, U.S. Pat. No. 4,708,871. Briefly, one may synthesize a set of overlapping oligopeptides derived from any selected calmodulin-binding peptide (e.g., $aa_1$–$aa_7$, $aa_2$–$aa_8$, $aa_3$–$aa_9$, etc.) bound to a solid phase array of pins, with a unique oligopeptide on each pin. The pins are arranged to match the format of a 96-well microtiter plate, permitting one to assay all pins simultaneously, e.g., for binding to labeled calmodulin. Using this method, one may readily determine the binding affinity for calmodulin for every possible subset of consecutive amino acids presented in any selected calmodulin-binding peptide of the invention.

Analogs of the invention are also prepared by standard solid-phase methods, and those methods described in PCT application US91/04282.

Many proteins may be modified at either the C- or N-terminus by adding a short oligopeptide without adversely affecting the protein's normal biological activity. Thus, proteins modified by addition of a calmodulin-binding peptide of the invention should retain their native activities, and additionally bind calmodulin. Such peptide-modified proteins may be purified by affinity chromatography using a column derivatized with calmodulin, such as calmodulin-Sepharose®. The calmodulin-binding sequence may also be inserted near a ligand binding site already present in the native protein, such that binding of calmodulin obscures the ligand binding site. Thus, one may prepare proteins which are additionally regulated or inhibited by calmodulin and $Ca^{2+}$.

Additionally, one may insert a calmodulin-binding sequence into antibodies (e.g., in the Fc region) in order to direct the calmodulin-inhibitory activity to a particular target tissue. For example, antibody structure is relatively well-characterized. One may insert or replace a portion of the Fc region of a monoclonal antibody (MAb) with one or more calmodulin-binding sequences by homologous recombination of the antibody gene, or by other standard genetic engineering techniques, in order to provide a MAb having calmodulin-inhibitory activity. MAbs selective for tumor-associated antigens may thus be endowed with chemotherapeutic activity. Similarly, MAbs selective for eukaryotic pathogens may be made capable of inhibiting or killing the pathogens.

Peptides of the invention are preferably administered topically or by parenteral means, including subcutaneous and intramuscular injection, implantation of sustained release depots, intravenous injection, intranasal administration, and the like. Accordingly, the peptides may be administered as a pharmaceutical composition comprising one or more peptides in combination with a pharmaceutically acceptable excipient. Such compositions may be aqueous solutions, emulsions, creams, ointments, suspensions, gels, liposomal suspensions, and the like. Suitable excipients include water, saline, Ringer's solution, dextrose solution, and solutions of ethanol, glucose, sucrose, dextran, mannose, mannitol, sorbitol, polyethylene glycol (PEG), phosphate, acetate, gelatin, collagen, Carbopol®, vegetable oils, and the like. One may additionally include suitable preservatives, stabilizers, antioxidants, antimicrobials, and buffering agents, for example, BHA, BHT, citric acid, ascorbic acid, tetracycline, and the like. Cream or ointment bases useful in formulation include lanolin, Silvadene® (Marion), Aquaphor® (Duke Laboratories), and the like. Alternatively, one may incorporate or encapsulate peptides of the invention in a suitable polymer matrix or membrane, thus providing a sustained-release delivery device suitable for implantation near the site to be treated locally. Other devices include indwelling catheters and devices such as the Alzet® minipump. Ophthalmic preparations may be formulated using commercially available vehicles such as Sorbi-care® (Allergan), Neodecadron® (Merck, Sharp & Dohme), Lacrilube®, and the like. Further, one may provide the peptides in solid form, especially as a lyophilized powder. Lyophilized formulations typically contain stabilizing and bulking agents, for example human serum albumin, sucrose, mannitol, and the like. A thorough discussion of pharmaceutically acceptable excipients is available in *Remington's Pharmaceutical Sciences* (Mack Pub. Co.). The peptides/fragments/analogs of the invention may be further modified to improve cellular uptake by estefification. The charged residues may be masked by esterifying carboxylic acid groups with acetoxymethyl in order to facilitate diffusion through the plasma membrane. Once inside the cell, endogenous nonspecific esterases saponify the acetoxymethyl group readily, thus regenerating the native form of the calmodulin-binding peptide.

The amount of calmodulin-binding peptide required to treat any particular disorder will of course vary depending upon the nature and severity of the disorder, the age and condition of the subject, and other factors readily determined by one of ordinary skill in the art. The appropriate dosage may be determined by one of ordinary skill in the art.

For example, for prevention of pregnancy, an amount of calmodulin-binding peptide administered intrauterally may range from about 2 μg/kg to about 10 mg/kg. An appropriate dose for treatment of tumors will range from about 2 μg/kg to about 20 mg/kg.

In general, peptides of the invention will be useful for control of cell growth, division, and meiosis; regulation of cell motility (such as chemotaxis, endocytosis), sperm motility, and smooth muscle motility (e.g., cardiac muscle, gut muscle); prevention of pregnancy; regulation of carbohydrate metabolism (e.g., regulation of glucose and/or glycogen metabolism); regulation of neurotransmission (e.g., exocytosis at synaptic junctions); anti-psychotic activity; anti-inflammatory activity (e.g., through regulation of the lipoxygen lipase pathway); regulation of secretory processes; and regulation of fluid secretion.

C. EXAMPLES

The example presented below is provided as a further guide to the practitioner of ordinary skill in the art, and is not to be construed as limiting the invention in any way.

Example (Selection of Peptides)

A.) Preparation: Calmodulin (prepared from rat testes) was coupled to CNBr-activated Sepharose® 4B beads following the manufacturer's directions to prepare a 1 mL column, and the column stripped with 6M guanidine.HCl. A 50 μL aliquot of random peptide bacteriophage library ($5\times10^{10}$ phage, obtained from James Devlin, Chiron Corporation) was diluted in 1 mL of sterile column buffer (50 mM Tris.HCl, 1 mg/mL BSA, pH 7.5) containing 1 mM $CaCl_2$, and the solution applied to the calmodulin-Sepharose® column preequilibrated with column buffer containing 1 mM $CaCl_2$. The bacteriophage library is further described in J.J. Devlin et al., Science (1990) 249:404–06, which also describes preparation and screening. See also S.F. Parmley and G.P. Smith, Gene (1988) 73:305.

B.) Elution/Selection: The column was then washed with column buffer containing 1 mM $CaCl_2$ (25 mL), then column buffer containing 1 mM CaCh and 1 M NaCl (50 mL), then column buffer containing 1 mM EGTA and 1M NaCl (25 mL), and finally with 0.1M glycine.HCl, pH 2.2, containing 1 mg/mL BSA (25 mL). Fractions were collected for each elution with EGTA or glycine. Following the final elution, the column was again stripped with 6M guanidine-.HCl.

Fractions eluted with EGTA were neutralized by adding $CaCl_2$ to a final concentration of 1 mM. Fractions eluted with glycine were neutralized by adding 1M Tris base to a final pH of 7.5. The numbers of bacteriophage in fractions were determined by standard microbiological procedures.

C.) Amplification: EGTA-eluted fractions were pooled, and the phage amplified in XL-1 Blue E. coli on solid media (density ≦20,000 phage per 75 $cm^2$). The phage were harvested by adding sterile SM (100 mM NaCl, 7.5 mM $MgSO_4$, 50 mM Tris, 0.01% gelatin, pH 7.5), and incubating at 4° C. overnight. SM containing phage was removed from the amplification plates, and residual bacteria removed by centrifugation at 10,000×g for 10 min. An aliquot of the resulting enriched, amplified phage (5–10×$10^{10}$ pfu) was applied to the calmodulin-Sepharose® column, and reselected and eluted as described in part B) above twice more. After the third application to the calmodulin-Sepharose® column, individual bacteriophage clones were selected from the final EGTA eluate, and the sequences of the random DNA inserts (within the pIII protein) were determined by standard DNA sequencing methods.

Glycine-eluted fractions were also pooled, and treated in parallel with the EGTA-eluted fractions, as described above. The sequences of the random DNA inserts were determined by standard DNA sequencing methods.

D.) Results: The sequences obtained are listed below in single-letter amino acid code. The first two amino acids, alanine-glutamic acid ("AE"), are derived from the bacteriophage pIII protein immediately preceding the random insert. The six proline residues at the C-terminus are inserted to extend the random insert away from the pIII protein to maximize accessibility for binding, and to minimize any secondary structure that might otherwise be imposed on the random insert by the pIII protein.

AE-SFKQLVTEVFLQSRH-PPPPPP (SEQ ID NO. 31);
AE-PWLKIRDSLQLNYLP-PPPPPP (SEQ ID NO. 32);
AE-GSWLQLLNLMKQMNN-PPPPPP (SEQ ID NO. 33);
AE-ASWTTVRSHFGSTMQ-PPPPPP (SEQ ID NO. 34);
AE-QLSWKALVTSVLSPT-PPPPPP (SEQ ID NO. 35);
AE-LSELWRNYSVRLMSS-PPPPPP (SEQ ID NO. 36);
AE-AQLNRWKSLSKTMMS-PPPPPP (SEQ ID NO. 37);
AE-TPSTSKWHQLIKSHR-PPPPPP (SEQ ID NO. 38);
AE-ISLPQLKWLTHRLKQ-PPPPPP (SEQ ID NO. 39);
AE-FPLLPYTWMARHHGS-PPPPPP (SEQ ID NO. 40);
AE-NLTPOYFKKWODLTK-PPPPPP (SEQ ID NO. 41);
AE-TSSLRNTLQYWRSLI-PPPPPP (SEQ ID NO. 42); AE-WPSLTEIKTLSHFSV-PPPPPP (SEQ ID NO. 43); AE-WPSISTLSTYTHSLH-PPPPPP (SEQ ID NO. 44); AE-WPSIHHMSHLLYSTY-PPPPPP (SEQ ID NO. 45); AE-WPSVRTILNTDLLHP-PPPPPP (SEQ ID NO. 46); AE-WPSPTRVISTTYFGS-PPPPPP (SEQ ID NO. 47); AE-WPSPHKIMSTLQYLR-PPPPPP (SEQ ID NO. 48); AE-WPTTRELRSLKSFLT-PPPPPP (SEQ ID NO. 49);
AE-WPKMTALQSTMKYVT-PPPPPP (SEQ ID NO. 50);
AE-WPKSFLMWMPKATOL-PPPPPP (SEQ ID NO. 51);
AE-WPRLSTLASMTNKAI-PPPPPP (SEQ ID NO. 52);
AE-WPRVKDLSTYLEGHV-PPPPPP (SEQ ID NO. 53);
AE-PWPMLKQLRLLKSSL-PPPPPP (SEQ ID NO. 54);
AE-PMNWPTVHAIRSLRK-PPPPPP (SEQ ID NO. 55);
AE-HISWPTLAQMSLMNF-PPPPPP (SEQ ID NO. 56);
AE-LAHWPPVKTVLRSFT-PPPPPP (SEQ ID NO. 57);
AE-VTKWPNLTQLRMLAT-PPPPPP (SEQ ID NO. 58);
and AE-GSTNRWPTVAKLMST-PPPPPP (SEQ ID NO. 59);

It is noteworthy that all but one of the sequences contains one or more tryptophan residues. Even more interesting is that all but four of the sequences contain one or more proline or glycine residues. Many have a proline residue (i.e., a "helix breaker") adjacent to the tryptophan. The presence of proline and/or glycine residues in a peptide generally inhibits the formation of an alpha helix. Thus, the peptides of the invention are unusual because they do not follow current predictions that calmodulin-binding peptides should adopt a strict alpha helix conformation.

5,585,475

What is claimed:

1. A peptide capable of inhibiting calmodulin, said peptide selected from the group consisting of:
   (a) an oligopeptide having the sequence shown in SEQ ID NO: 1, 2, 3, 4, 5, 6, 7, 8, 9, 10, 11, 12, 13, 14, 15, 16, 17, 18, 19, 20, 21, 22, 23, 24, 25, 26, 27, 28, or 29;
   (b) an active fragment of the oligopeptide of (a), wherein said active fragment comprises at least eight consecutive residues of said sequence, and wherein said active fragment exhibits $K_D \leq 50$ nM for binding to calmodulin under physiological conditions; and
   (c) an analog of the oligopeptide of (a), wherein said analog differs from the oligopeptide of (a) only by the conservative replacement of one or two amino acid residues in said sequence by other amino acid residues, and wherein said analog exhibits $K_D \leq 50$ nM for binding to calmodulin under physiological conditions;
   or a pharmaceutically acceptable salt, ester, amide, or anhydride thereof.

2. A peptide according to claim 1, wherein said oligopeptide of (a) has the sequence shown in SEQ ID NO: 13, 14, 15, 16, 17, 18, 19, 20, 21, 22, 23, 24, 25, 26, 27, 28, or 29; or a pharmaceutically acceptable salt, ester, amide, or anhydride thereof.

3. A protein capable of inhibiting calmodulin, wherein the sequence of said protein comprises the amino acid sequence of a peptide according to claim 1.

4. A protein according to claim 3, wherein said oligopeptide of (a) has the sequence shown in SEQ ID NO: 13, 14, 15, 16, 17, 18, 19, 20, 21, 22, 23, 24, 25, 26, 27, 28, or 29.

5. A compound of the formula:

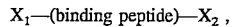

wherein $X_1$ and $X_2$ are independently selected from the group consisting of a peptide of 1–200 amino acids, acyl, and H; and wherein said binding peptide has the amino acid sequence of a peptide according to claim 1;
or a pharmaceutically acceptable salt, ester, amide, or anhydride thereof.

6. An oligonucleotide which encodes the amino acid sequence of a peptide according to claim 1.

* * * * *

SEQUENCE LISTING ( 1 ) GENERAL INFORMATION:

( i i i ) NUMBER OF SEQUENCES: 59

( 2 ) INFORMATION FOR SEQ ID NO:1:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

```
Ser  Phe  Lys  Gln  Leu  Val  Thr  Glu  Val  Phe  Leu  Gln  Ser  Arg  His
1                   5                        10                       15
```

( 2 ) INFORMATION FOR SEQ ID NO:2:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

```
Pro  Trp  Leu  Lys  Ile  Arg  Asp  Ser  Leu  Gln  Leu  Asn  Tyr  Leu  Pro
1                   5                        10                       15
```

( 2 ) INFORMATION FOR SEQ ID NO:3:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:3:

```
Gly  Ser  Trp  Leu  Gln  Leu  Leu  Asn  Leu  Met  Lys  Gln  Met  Asn  Asn
1                   5                        10                       15
```

( 2 ) INFORMATION FOR SEQ ID NO:4:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:4:

```
Ala  Ser  Trp  Thr  Thr  Val  Arg  Ser  His  Phe  Gly  Ser  Thr  Met  Gln
1                   5                        10                       15
```

( 2 ) INFORMATION FOR SEQ ID NO:5:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:5:

Gln Leu Ser Trp Lys Ala Leu Val Thr Ser Val Leu Ser Pro Thr
1               5                   10                  15

( 2 ) INFORMATION FOR SEQ ID NO:6:

( i ) SEQUENCE CHARACTERISTICS:
         ( A ) LENGTH: 15 amino acids
         ( B ) TYPE: amino acid
         ( C ) STRANDEDNESS: single
         ( D ) TOPOLOGY: linear ( i i ) MOLECULE TYPE: peptide ( x i ) SEQUENCE DESCRIPTION: SEQ ID NO:6:

Leu Ser Glu Leu Trp Arg Asn Tyr Ser Val Arg Leu Met Ser Ser
1               5                   10                  15

( 2 ) INFORMATION FOR SEQ ID NO:7:

( i ) SEQUENCE CHARACTERISTICS:
         ( A ) LENGTH: 15 amino acids
         ( B ) TYPE: amino acid
         ( C ) STRANDEDNESS: single
         ( D ) TOPOLOGY: linear ( i i ) MOLECULE TYPE: peptide ( x i ) SEQUENCE DESCRIPTION: SEQ ID NO:7:

Ala Gln Leu Asn Arg Trp Lys Ser Leu Ser Lys Thr Met Met Ser
1               5                   10                  15

( 2 ) INFORMATION FOR SEQ ID NO:8:

( i ) SEQUENCE CHARACTERISTICS:
         ( A ) LENGTH: 15 amino acids
         ( B ) TYPE: amino acid
         ( C ) STRANDEDNESS: single
         ( D ) TOPOLOGY: linear ( i i ) MOLECULE TYPE: peptide ( x i ) SEQUENCE DESCRIPTION: SEQ ID NO:8:

Thr Pro Ser Thr Ser Lys Trp His Gln Leu Ile Lys Ser His Arg
1               5                   10                  15

( 2 ) INFORMATION FOR SEQ ID NO:9:

( i ) SEQUENCE CHARACTERISTICS:
         ( A ) LENGTH: 15 amino acids
         ( B ) TYPE: amino acid
         ( C ) STRANDEDNESS: single
         ( D ) TOPOLOGY: linear ( i i ) MOLECULE TYPE: peptide ( x i ) SEQUENCE DESCRIPTION: SEQ ID NO:9:

Ile Ser Leu Pro Gln Leu Lys Trp Leu Thr His Arg Leu Lys Gln
1               5                   10                  15

( 2 ) INFORMATION FOR SEQ ID NO:10:

( i ) SEQUENCE CHARACTERISTICS:
         ( A ) LENGTH: 15 amino acids
         ( B ) TYPE: amino acid
         ( C ) STRANDEDNESS: single
         ( D ) TOPOLOGY: linear ( i i ) MOLECULE TYPE: peptide ( x i ) SEQUENCE DESCRIPTION: SEQ ID NO:10:

```
Phe  Pro  Leu  Leu  Pro  Tyr  Thr  Trp  Met  Ala  Arg  His  His  Gly  Ser
1                  5                        10                        15
```

( 2 ) INFORMATION FOR SEQ ID NO:11:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:11:

```
Asn  Leu  Thr  Pro  Gln  Tyr  Phe  Lys  Lys  Trp  Gln  Asp  Leu  Thr  Lys
1                  5                        10                        15
```

( 2 ) INFORMATION FOR SEQ ID NO:12:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:12:

```
Thr  Ser  Ser  Leu  Arg  Asn  Thr  Leu  Gln  Tyr  Trp  Arg  Ser  Leu  Ile
1                  5                        10                        15
```

( 2 ) INFORMATION FOR SEQ ID NO:13:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:13:

```
Trp  Pro  Ser  Leu  Thr  Glu  Ile  Lys  Thr  Leu  Ser  His  Phe  Ser  Val
1                  5                        10                        15
```

( 2 ) INFORMATION FOR SEQ ID NO:14:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:14:

```
Trp  Pro  Ser  Ile  Ser  Thr  Leu  Ser  Thr  Tyr  Thr  His  Ser  Leu  His
1                  5                        10                        15
```

( 2 ) INFORMATION FOR SEQ ID NO:15:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:15:

Trp Pro Ser Ile His His Met Ser His Leu Leu Tyr Ser Thr Tyr
1               5                   10                  15

( 2 ) INFORMATION FOR SEQ ID NO:16:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:16:

Trp Pro Ser Val Arg Thr Ile Leu Asn Thr Asp Leu Leu His Pro
1               5                   10                  15

( 2 ) INFORMATION FOR SEQ ID NO:17:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:17:

Trp Pro Ser Pro Thr Arg Val Ile Ser Thr Thr Tyr Phe Gly Ser
1               5                   10                  15

( 2 ) INFORMATION FOR SEQ ID NO:18:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:18:

Trp Pro Ser Pro His Lys Ile Met Ser Thr Leu Gln Tyr Leu Arg
1               5                   10                  15

( 2 ) INFORMATION FOR SEQ ID NO:19:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:19:

Trp Pro Thr Thr Arg Glu Leu Arg Ser Leu Lys Ser Phe Leu Thr
1               5                   10                  15

( 2 ) INFORMATION FOR SEQ ID NO:20:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:20:

Trp Pro Lys Met Thr Ala Leu Gln Ser Thr Met Lys Tyr Val Thr
1               5                   10                  15

( 2 ) INFORMATION FOR SEQ ID NO:21:

( i ) SEQUENCE CHARACTERISTICS:
      ( A ) LENGTH: 15 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:21:

Trp Pro Lys Ser Phe Leu Met Trp Met Pro Lys Ala Thr Gln Leu
1               5                   10                  15

( 2 ) INFORMATION FOR SEQ ID NO:22:

( i ) SEQUENCE CHARACTERISTICS:
      ( A ) LENGTH: 15 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:22:

Trp Pro Arg Leu Ser Thr Leu Ala Ser Met Thr Asn Lys Ala Ile
1               5                   10                  15

( 2 ) INFORMATION FOR SEQ ID NO:23:

( i ) SEQUENCE CHARACTERISTICS:
      ( A ) LENGTH: 15 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:23:

Trp Pro Arg Val Lys Asp Leu Ser Thr Tyr Leu Glu Gly His Val
1               5                   10                  15

( 2 ) INFORMATION FOR SEQ ID NO:24:

( i ) SEQUENCE CHARACTERISTICS:
      ( A ) LENGTH: 15 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:24:

Pro Trp Pro Met Leu Lys Gln Leu Arg Leu Leu Lys Ser Ser Leu
1               5                   10                  15

( 2 ) INFORMATION FOR SEQ ID NO:25:

( i ) SEQUENCE CHARACTERISTICS:
      ( A ) LENGTH: 15 amino acids
      ( B ) TYPE: amino acid
      ( C ) STRANDEDNESS: single
      ( D ) TOPOLOGY: linear ( i i ) MOLECULE TYPE: peptide ( x i ) SEQUENCE DESCRIPTION: SEQ ID NO:25:

Pro Met Asn Trp Pro Thr Val His Ala Ile Arg Ser Leu Arg Lys
1               5                   10                  15

( 2 ) INFORMATION FOR SEQ ID NO:26:

( i ) SEQUENCE CHARACTERISTICS:
    ( A ) LENGTH: 15 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:26:

His Ile Ser Trp Pro Thr Leu Ala Gln Met Ser Leu Met Asn Phe
1               5                   10                  15

( 2 ) INFORMATION FOR SEQ ID NO:27:

( i ) SEQUENCE CHARACTERISTICS:
    ( A ) LENGTH: 15 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:27:

Leu Ala His Trp Pro Pro Val Lys Thr Val Leu Arg Ser Phe Thr
1               5                   10                  15

( 2 ) INFORMATION FOR SEQ ID NO:28:

( i ) SEQUENCE CHARACTERISTICS:
    ( A ) LENGTH: 15 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:28:

Val Thr Lys Trp Pro Asn Leu Thr Gln Leu Arg Met Leu Ala Thr
1               5                   10                  15

( 2 ) INFORMATION FOR SEQ ID NO:29:

( i ) SEQUENCE CHARACTERISTICS:
    ( A ) LENGTH: 15 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:29:

Gly Ser Thr Asn Arg Trp Pro Thr Val Ala Lys Leu Met Ser Thr
1               5                   10                  15

( 2 ) INFORMATION FOR SEQ ID NO:30:

( i ) SEQUENCE CHARACTERISTICS:
    ( A ) LENGTH: 11 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:30:

```
Trp Pro Ser Leu Lys Gln Leu Arg Ser Leu Lys
1               5                   10
```

( 2 ) INFORMATION FOR SEQ ID NO:31:

- ( i ) SEQUENCE CHARACTERISTICS:
  - ( A ) LENGTH: 23 amino acids
  - ( B ) TYPE: amino acid
  - ( C ) STRANDEDNESS: single
  - ( D ) TOPOLOGY: linear ( i i ) MOLECULE TYPE: peptide ( x i ) SEQUENCE DESCRIPTION: SEQ ID NO:31:

```
Ala Glu Ser Phe Lys Gln Leu Val Thr Glu Val Phe Leu Gln Ser Arg
1               5                   10                  15
His Pro Pro Pro Pro Pro Pro
            20
```

( 2 ) INFORMATION FOR SEQ ID NO:32:

- ( i ) SEQUENCE CHARACTERISTICS:
  - ( A ) LENGTH: 23 amino acids
  - ( B ) TYPE: amino acid
  - ( C ) STRANDEDNESS: single
  - ( D ) TOPOLOGY: linear ( i i ) MOLECULE TYPE: peptide ( x i ) SEQUENCE DESCRIPTION: SEQ ID NO:32:

```
Ala Glu Pro Trp Leu Lys Ile Arg Asp Ser Leu Gln Leu Asn Tyr Leu
1               5                   10                  15
Pro Pro Pro Pro Pro Pro Pro
            20
```

( 2 ) INFORMATION FOR SEQ ID NO:33:

- ( i ) SEQUENCE CHARACTERISTICS:
  - ( A ) LENGTH: 23 amino acids
  - ( B ) TYPE: amino acid
  - ( C ) STRANDEDNESS: single
  - ( D ) TOPOLOGY: linear ( i i ) MOLECULE TYPE: peptide ( x i ) SEQUENCE DESCRIPTION: SEQ ID NO:33:

```
Ala Glu Gly Ser Trp Leu Gln Leu Leu Asn Leu Met Lys Gln Met Asn
1               5                   10                  15
Asn Pro Pro Pro Pro Pro Pro
            20
```

( 2 ) INFORMATION FOR SEQ ID NO:34:

- ( i ) SEQUENCE CHARACTERISTICS:
  - ( A ) LENGTH: 23 amino acids
  - ( B ) TYPE: amino acid
  - ( C ) STRANDEDNESS: single
  - ( D ) TOPOLOGY: linear ( i i ) MOLECULE TYPE: peptide ( x i ) SEQUENCE DESCRIPTION: SEQ ID NO:34:

```
Ala Glu Ala Ser Trp Thr Thr Val Arg Ser His Phe Gly Ser Thr Met
1               5                   10                  15
```

Gln Pro Pro Pro Pro Pro Pro
            20

( 2 ) INFORMATION FOR SEQ ID NO:35:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:35:

Ala Glu Gln Leu Ser Trp Lys Ala Leu Val Thr Ser Val Leu Ser Pro
1                 5                   10                  15

Thr Pro Pro Pro Pro Pro Pro
            20

( 2 ) INFORMATION FOR SEQ ID NO:36:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:36:

Ala Glu Leu Ser Glu Leu Trp Arg Asn Tyr Ser Val Arg Leu Met Ser
1                 5                   10                  15

Ser Pro Pro Pro Pro Pro Pro
            20

( 2 ) INFORMATION FOR SEQ ID NO:37:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:37:

Ala Glu Ala Gln Leu Asn Arg Trp Lys Ser Leu Ser Lys Thr Met Met
1                 5                   10                  15

Ser Pro Pro Pro Pro Pro Pro
            20

( 2 ) INFORMATION FOR SEQ ID NO:38:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:38:

Ala Glu Thr Pro Ser Thr Ser Lys Trp His Gln Leu Ile Lys Ser His
1                 5                   10                  15

Arg Pro Pro Pro Pro Pro Pro
            20

(2) INFORMATION FOR SEQ ID NO:39:

(i) SEQUENCE CHARACTERISTICS:
(A) LENGTH: 23 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:39:

```
Ala Glu Ile Ser Leu Pro Gln Leu Lys Trp Leu Thr His Arg Leu Lys
1               5                   10                  15
Gln Pro Pro Pro Pro Pro Pro
                20
```

(2) INFORMATION FOR SEQ ID NO:40:

(i) SEQUENCE CHARACTERISTICS:
(A) LENGTH: 23 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:40:

```
Ala Glu Phe Pro Leu Leu Pro Tyr Thr Trp Met Ala Arg His His Gly
1               5                   10                  15
Ser Pro Pro Pro Pro Pro Pro
                20
```

(2) INFORMATION FOR SEQ ID NO:41:

(i) SEQUENCE CHARACTERISTICS:
(A) LENGTH: 23 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:41:

```
Ala Glu Asn Leu Thr Pro Gln Tyr Phe Lys Lys Trp Gln Asp Leu Thr
1               5                   10                  15
Lys Pro Pro Pro Pro Pro Pro
                20
```

(2) INFORMATION FOR SEQ ID NO:42:

(i) SEQUENCE CHARACTERISTICS:
(A) LENGTH: 23 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:42:

```
Ala Glu Thr Ser Ser Leu Arg Asn Thr Leu Gln Tyr Trp Arg Ser Leu
1               5                   10                  15
Ile Pro Pro Pro Pro Pro Pro
                20
```

(2) INFORMATION FOR SEQ ID NO:43:

(i) SEQUENCE CHARACTERISTICS:
(A) LENGTH: 23 amino acids (B) TYPE: amino acid
(C) STRANDEDNESS: single
(D) TOPOLOGY: linear (ii) MOLECULE TYPE: peptide (xi) SEQUENCE DESCRIPTION: SEQ ID NO:43:

```
Ala Glu Trp Pro Ser Leu Thr Glu Ile Lys Thr Leu Ser His Phe Ser
1               5                   10                  15
Val Pro Pro Pro Pro Pro Pro
            20
```

(2) INFORMATION FOR SEQ ID NO:44:

(i) SEQUENCE CHARACTERISTICS:
(A) LENGTH: 23 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:44:

```
Ala Glu Trp Pro Ser Ile Ser Thr Leu Ser Thr Tyr Thr His Ser Leu
1               5                   10                  15
His Pro Pro Pro Pro Pro Pro
            20
```

(2) INFORMATION FOR SEQ ID NO:45:

(i) SEQUENCE CHARACTERISTICS:
(A) LENGTH: 23 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:45:

```
Ala Glu Trp Pro Ser Ile His His Met Ser His Leu Leu Tyr Ser Thr
1               5                   10                  15
Tyr Pro Pro Pro Pro Pro Pro
            20
```

(2) INFORMATION FOR SEQ ID NO:46:

(i) SEQUENCE CHARACTERISTICS:
(A) LENGTH: 23 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:46:

```
Ala Glu Trp Pro Ser Val Arg Thr Ile Leu Asn Thr Asp Leu Leu His
1               5                   10                  15
Pro Pro Pro Pro Pro Pro Pro
            20
```

(2) INFORMATION FOR SEQ ID NO:47:

(i) SEQUENCE CHARACTERISTICS:
(A) LENGTH: 23 amino acids
(B) TYPE: amino acid
(C) STRANDEDNESS: single
(D) TOPOLOGY: linear ( i i ) MOLECULE TYPE: peptide ( x i ) SEQUENCE DESCRIPTION: SEQ ID NO:47:

Ala Glu Trp Pro Ser Pro Thr Arg Val Ile Ser Thr Thr Tyr Phe Gly
1               5                   10                  15

Ser Pro Pro Pro Pro Pro Pro
            20

( 2 ) INFORMATION FOR SEQ ID NO:48:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:48:

Ala Glu Trp Pro Ser Pro His Lys Ile Met Ser Thr Leu Gln Tyr Leu
1               5                   10                  15

Arg Pro Pro Pro Pro Pro Pro
            20

( 2 ) INFORMATION FOR SEQ ID NO:49:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:49:

Ala Glu Trp Pro Thr Thr Arg Glu Leu Arg Ser Leu Lys Ser Phe Leu
1               5                   10                  15

Thr Pro Pro Pro Pro Pro Pro
            20

( 2 ) INFORMATION FOR SEQ ID NO:50:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:50:

Ala Glu Trp Pro Lys Met Thr Ala Leu Gln Ser Thr Met Lys Tyr Val
1               5                   10                  15

Thr Pro Pro Pro Pro Pro Pro
            20

( 2 ) INFORMATION FOR SEQ ID NO:51:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:51:

```
        Ala  Glu  Trp  Pro  Lys  Ser  Phe  Leu  Met  Trp  Met  Pro  Lys  Ala  Thr  Gln
        1              5                        10                       15

Leu  Pro  Pro  Pro  Pro  Pro  Pro
                        20
```

( 2 ) INFORMATION FOR SEQ ID NO:52:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:52:

```
        Ala  Glu  Trp  Pro  Arg  Leu  Ser  Thr  Leu  Ala  Ser  Met  Thr  Asn  Lys  Ala
        1              5                        10                       15

Ile  Pro  Pro  Pro  Pro  Pro  Pro
                        20
```

( 2 ) INFORMATION FOR SEQ ID NO:53:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:53:

```
        Ala  Glu  Trp  Pro  Arg  Val  Lys  Asp  Leu  Ser  Thr  Tyr  Leu  Glu  Gly  His
        1              5                        10                       15

Val  Pro  Pro  Pro  Pro  Pro  Pro
                        20
```

( 2 ) INFORMATION FOR SEQ ID NO:54:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:54:

```
        Ala  Glu  Pro  Trp  Pro  Met  Leu  Lys  Gln  Leu  Arg  Leu  Leu  Lys  Ser  Ser
        1              5                        10                       15

Leu  Pro  Pro  Pro  Pro  Pro  Pro
                        20
```

( 2 ) INFORMATION FOR SEQ ID NO:55:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:55:

```
        Ala  Glu  Pro  Met  Asn  Trp  Pro  Thr  Val  His  Ala  Ile  Arg  Ser  Leu  Arg
        1              5                        10                       15

Lys  Pro  Pro  Pro  Pro  Pro  Pro
```

( 2 ) INFORMATION FOR SEQ ID NO:56:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:56:

```
Ala  Glu  His  Ile  Ser  Trp  Pro  Thr  Leu  Ala  Gln  Met  Ser  Leu  Met  Asn
1                   5                        10                       15
Phe  Pro  Pro  Pro  Pro  Pro  Pro
                20
```

( 2 ) INFORMATION FOR SEQ ID NO:57:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:57:

```
Ala  Glu  Leu  Ala  His  Trp  Pro  Pro  Val  Lys  Thr  Val  Leu  Arg  Ser  Phe
1                   5                        10                       15
Thr  Pro  Pro  Pro  Pro  Pro  Pro
                20
```

( 2 ) INFORMATION FOR SEQ ID NO:58:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:58:

```
Ala  Glu  Val  Thr  Lys  Trp  Pro  Asn  Leu  Thr  Gln  Leu  Arg  Met  Leu  Ala
1                   5                        10                       15
Thr  Pro  Pro  Pro  Pro  Pro  Pro
                20
```

( 2 ) INFORMATION FOR SEQ ID NO:59:

( i ) SEQUENCE CHARACTERISTICS:
        ( A ) LENGTH: 23 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:59:

```
Ala  Glu  Gly  Ser  Thr  Asn  Arg  Trp  Pro  Thr  Val  Ala  Lys  Leu  Met  Ser
1                   5                        10                       15
Thr  Pro  Pro  Pro  Pro  Pro  Pro
                20
```